(12) United States Patent
Virno et al.

(10) Patent No.: US 8,822,429 B2
(45) Date of Patent: Sep. 2, 2014

(54) CITICOLINE FOR THE TREATMENT OF GLAUCOMA AND OCULAR HYPERTENSION

(75) Inventors: Cristiano Virno, Rome (IT); Marco Malizia, Rome (IT)

(73) Assignee: Omikron Italia S.r.l., Rome (IT)

( * ) Notice: Subject to any disclaimer, the term of this patent is extended or adjusted under 35 U.S.C. 154(b) by 37 days.

(21) Appl. No.: 13/580,181

(22) PCT Filed: Feb. 17, 2011

(86) PCT No.: PCT/IB2011/050663
§ 371 (c)(1),
(2), (4) Date: Aug. 21, 2012

(87) PCT Pub. No.: WO2011/101802
PCT Pub. Date: Aug. 25, 2011

(65) Prior Publication Data
US 2012/0316128 A1 Dec. 13, 2012

(30) Foreign Application Priority Data
Feb. 22, 2010 (IT) .............................. RM2010A0071

(51) Int. Cl.
*A61K 31/70* (2006.01)
*A61K 9/00* (2006.01)
*A61K 31/7068* (2006.01)

(52) U.S. Cl.
CPC ............ *A61K 9/0048* (2013.01); *A61K 31/7068* (2013.01)
USPC ................................................. 514/49; 514/52

(58) Field of Classification Search
None
See application file for complete search history.

(56) References Cited

U.S. PATENT DOCUMENTS 5,773,472 A * 6/1998 Stjernschantz et al. ....... 514/530

OTHER PUBLICATIONS

Oshitari et al., Neuroreport, vol. 13 (16), Nov. 2002, pp. 2109-2111.*
Wikipedia—Definition for "Route of Administration", Nov. 2013.*
Oshitari et al. "Citicoline has a protective effect on damaged retinal ganglion cells in mouse culture retina" *Neuroreport*, vol. 13, No. 16, pp. 2109-2111 (Nov. 2002).
Int'l Search Report for PCT/IB2011/050663, one page, mailed Jun. 8, 2011.
Written Opinion for PCT/IB2011/050663, seven pages, mailed Jun. 8, 2011.
International Preliminary Report on Patentability for PCT/IB2011/050663, 14 pages, mailed Apr. 26, 2011.

* cited by examiner

*Primary Examiner* — Traviss C McIntosh, III
(74) *Attorney, Agent, or Firm* — Nixon & Vanderhye PC

(57) ABSTRACT

The present invention refers to citicoline and to compositions containing it for topic use in treating glaucoma and/or ocular hypertension.

14 Claims, 11 Drawing Sheets

CITICOLINE FOR THE TREATMENT OF GLAUCOMA AND OCULAR HYPERTENSION

Figure 1:
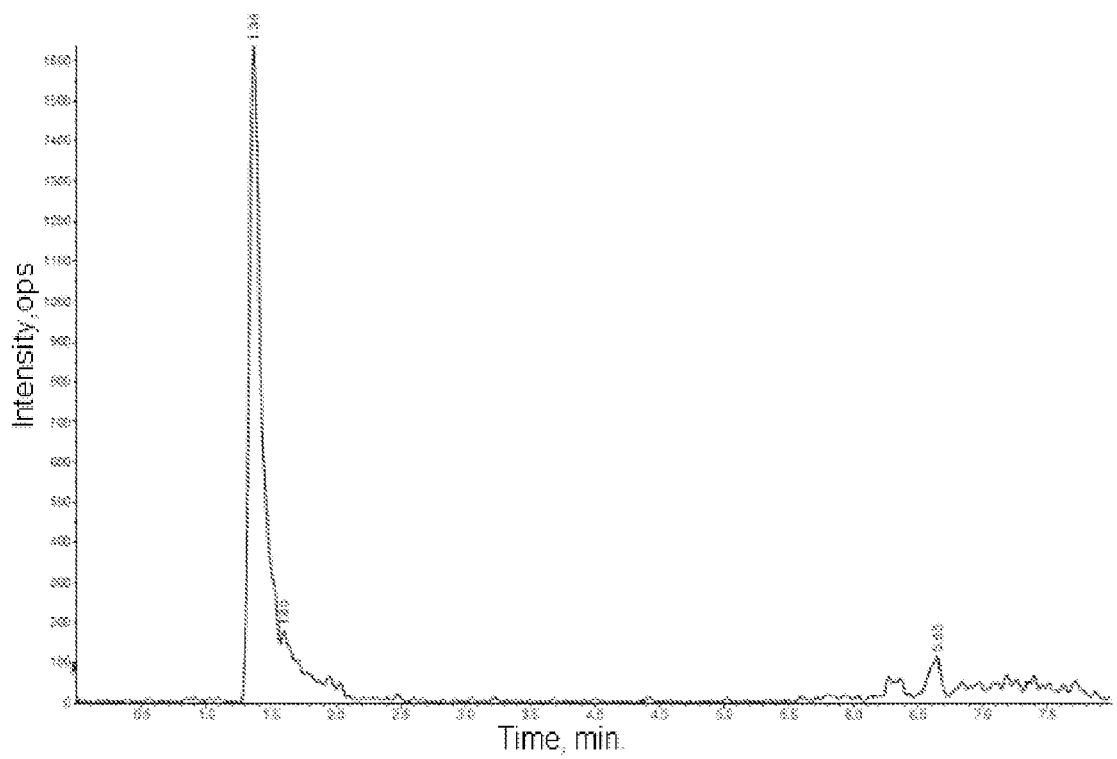

This application is the U.S. national phase of International Application No. PCT/IB2011/050663, filed 17 Feb. 2011, which designated the U.S. and claims priority to Application No. IT RM2010A000071, filed 22 Feb. 2010; the entire contents of each of which are hereby incorporated by reference.

DESCRIPTION

The present invention refers to citicoline and to compositions containing it for topic use in treating glaucoma and/or ocular hypertension.

STATE OF THE PRIOR ART

Glaucoma is a chronic neurodegenerative pathology characterized by progressive loss of retinal ganglion cells and structural changes of the optic nerve head. It represents the second leading cause of blindness worldwide. The most common form, open-angle primary glaucoma, has as main risk factor the increase of intraocular pressure (IOP), therefore the first therapeutic approach is represented by hypotonizing topic drugs. However, since more than one-third of the patients, despite being under good pressure control, delay yet do not stop vision damage progression, other non pressure-dependent mechanisms are deemed to be involved (Grieb P et al. J Neurosci Res 2002). Specifically, following a primary insult of hyperbaric nature, neuron apoptosis is triggered, which interferes with normal blood supply at the level of the capillary district of this structure, and regular axonal transport, anterograde as well as retrograde, of metabolites and neurotrophins indispensable for ganglionar cell survival is compromised. Apoptosis is accountable for the secondary insult linked to local excitotoxicity mechanisms due to hyperstimulation of the NMDA receptors by glutamate freed from apoptotic cells. Glutamate, in fact, when present in excessive concentrations in the extracellular space, hyperstimulates NMDA receptors on the surface of the surrounding neurons, which cause the opening of $Ca^{++}$ channels. Hyperafflux of $Ca^{++}$ ions in the cell represents the trigger of the biochemical cascade that will lead to apoptosis of the neuron itself, configuring a mechanism capable of self-feeding also in the absence of the primary insult. Another key step in the cell damage mechanism in the course of apoptosis is represented by hyperactivation of phospholipase A2, an enzyme able to destabilize and disgregate the cell membrane through catabolism of its main constituent, the phosphatidylcoline phospholipid (Burgoyne F C et al., Prog Retin Eye Res 2005; 24). Evidently, ocular hypotonization has scanty effects on the secondary insult representing a real death cascade accountable for damage progression. In the neuroprotection field, particular interest is addressed to the citicoline (cytidine-5'-diphosphocholine) molecule, for its action mechanism and the scientific evidence going from experimental studies to clinical trials on glaucomatous patients.

Citicoline (cytidine-5'-diphosphocholine) is a natural precursor of phosphatidylcholine, main component of neuronal and mitochondrial membranes. Taken orally, it is rapidly absorbed and less than 1% of it is excreted in the feces. Plasma peak is reached 1 hour after ingestion, followed by a larger peak 24 h later. It is metabolized in the intestinal wall and in the liver. Coline and citidine, deriving from hydrolysis of the same molecule, are absorbed by systemic circulation and separately cross the blood-brain barrier (BEE) for resynthesis into citicoline (cytidine-5'-diphosphocholine) at the brain level. Elimination mostly occurs via the respiratory route and urinary excretion, mirroring the two plasma peaks, i.e. a first rapid elimination, followed by a slower one (Citicoline, monograph Altern Med Rev 2008).

At the brain level citicoline mainly acts as substrate for phosphatidylcholine formation and as phospholipase A2 inhibitor, therefore having a direct action on the membrane damage of the still viable neuron. Moreover, this molecule exhibits a neuromodulating action mainly at the level of the dopaminergic system, which offers the rationale for citicoline use in treating Parkinson's disease, as well as glaucoma, dopamine being one of the main neurotransmitters involved in the transmission of the visual signal, both at a retinal and post-retinal level.

Numerous studies in literature demonstrate the positive effect of citicoline on glaucomatous patients, both on the visual field, by computerized campimetry, (Pecori Giraldi et al 1989) and on the entire visual pathway, by use of pattern electroretinogram (PERG) and visual evoked potentials (VEP) (Parisi et al 1999, 2005, 2008, Rejadak et al 2003).

In particular, the studies by Parisi and collaborators confirm the same results in glaucomatous patients under hypotonizing therapy and with citicoline administered both intramuscularly (1000 mg/die) and orally (1600 mg/die), with respect to glaucomatous patients under hypotonizing therapy only, and the need to cyclically repeat the treatment in order to maintain the positive effects on the visual function (overall study time, 8 years).

In 2009, Chan et al. published the results of in vivo use of magnetic resonance spectroscopy (proton magnetic resonance spectroscopy $^1H$ MRS) on experimental models of glaucoma in rat, demonstrating that glaucoma is also characterized by alteration of coline metabolism at the level of the visual cortex, mirroring the compromission of the structural integrity of the neuronal membranes.

Intramuscular administration of citicoline for treating glaucoma is clearly very uncomfortable for the patient and does not allow use of the substance over the long periods needed to have the positive results observed by the studies. Intramuscular administration, besides the discomfort of not being self-done and the entailed need for patients to have a person capable of doing intramuscular injections available, need that, above all in aged patients, might be hard to meet, can expose to the risk of infective complications following chronic therapy.

Oral administration of citicoline for treating glaucoma, though representing a step forward with respect to intramuscular therapy, is conditioned by the difficulties due to the impossibility of use in subjects having gastric or intestinal pathologies, as well as by the low concentration of active principle arriving at the level of the optic nerve head, the nervous structure mostly damaged by glaucoma pathology owing to metabolization in the liver.

Oshitari et al. (Neuroreport 2002) evaluated the neurite regeneration effect in vitro obtained by adding citicoline to cultured retinal ganglion cells (RGCs) obtained from explanted mouse retinas.

Therefore, in light of the foregoing, the need to propose new therapeutic strategies of neuroprotective type for treating glaucoma was greatly felt.

SUMMARY OF THE INVENTION

Studies performed by the present Inventors on an in vivo experimental model surprisingly demonstrated that citicoline administration on the ocular surface is ideal to ensure the passage of the active principle into the posterior segment of the eye (vitreous chamber) and the reaching of the retina and optic nerve head.

One of the essential features of the invention is represented by the fact that a substance like citicoline, having a neuroprotective activity on retina and optic nerve, has never been used topically; in fact, it has to be taken into account that to date citicoline had only been IM- (intramuscularly), IV- (intravenously) or orally administered, and in no way was it foreseeable that citicoline administered on the ocular surface were able to cross the barriers within the cornea, made impermeable to many active principles by the presence of gap junctions interconnecting the cells of corneal epithelium, conjunctiva, sclera and trabeculate, and thereby reach retina and optic nerve head.

Therefore, object of the present invention is citicoline for topic use in treating glaucoma and/or ocular hypertension.

Object of the invention are also compositions for topic use in treating glaucoma and/or ocular hypertension, comprising citicoline and one or more carriers and/or diluents and/or excipients.

The present invention entails a series of advantages in the therapy against glaucoma, one of the main causes of blindness worldwide, and ocular hypertension:

The ease of administration in comparison with the pharmaceutical forms currently known for citicoline;

A lower concentration of active principle required for achieving therapeutic target, retina and optic nerve, both for arrival directly on the site of action and above all, because by this way are avoided the hepatic and renal filters, which metabolize a large part of the active principle and thereby significantly reduce pharmacological activity.

A further advantage of the invention is represented by the possibility of administering the active principle plural times during the day, thereby allowing not only to reach high values of active principle at the retina level but also to easily maintain them, something which is it also impossible to have with the administration routes used to date. In fact, by the intramuscular route it is easily understandable how it is not thinkable that long-lasting therapies may be carried out with repeated injections in the course of the day, whereas by the oral route the problems, besides those of compliance for the patient, are related to possible gastrointestinal complications due to chronic therapy.

The advantages, features and modes of employ of the present invention will be made apparent in the following detailed description of some embodiments thereof, given by way of example and not for limitative purposes.

DETAILED DESCRIPTION OF THE FIGURES

FIG. 1. HPLC profile obtained by analyzing a sample of the right eye of a mouse treated with a solution based on 2% citicoline, 0.2% hyaluronic acid and 0.01% BAK, as described in the examples. Analyzed sample profile shows the presence of a peak at an elution time of 1.36 minutes, corresponding to citicoline. In this experiment it is demonstrated the presence of significant amounts of citicoline in the posterior chamber of the treated eye.

Figure 2:
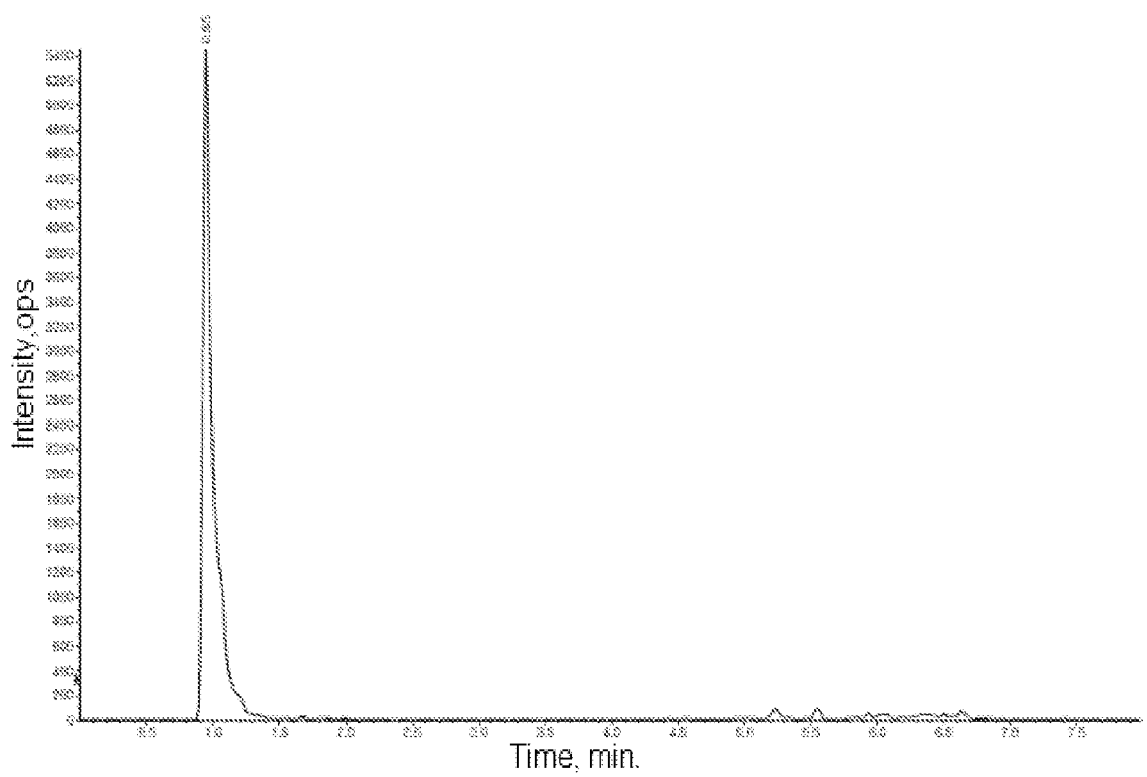

FIG. 2. HPLC profile obtained by analyzing a sample of the left (contralateral) eye of a mouse treated with a solution based on 2% citicoline, 0.2% hyaluronic acid and 0.01% BAK, as described in the examples. Analyzed sample profile shows the presence of a peak at an elution time of 0.95 minutes, corresponding to citicoline. In this experiment it is demonstrated the presence of significant amounts of citicoline in the posterior chamber of the contralateral eye, thereby assuming systemic absorption through the trabeculate.

Figure 3:
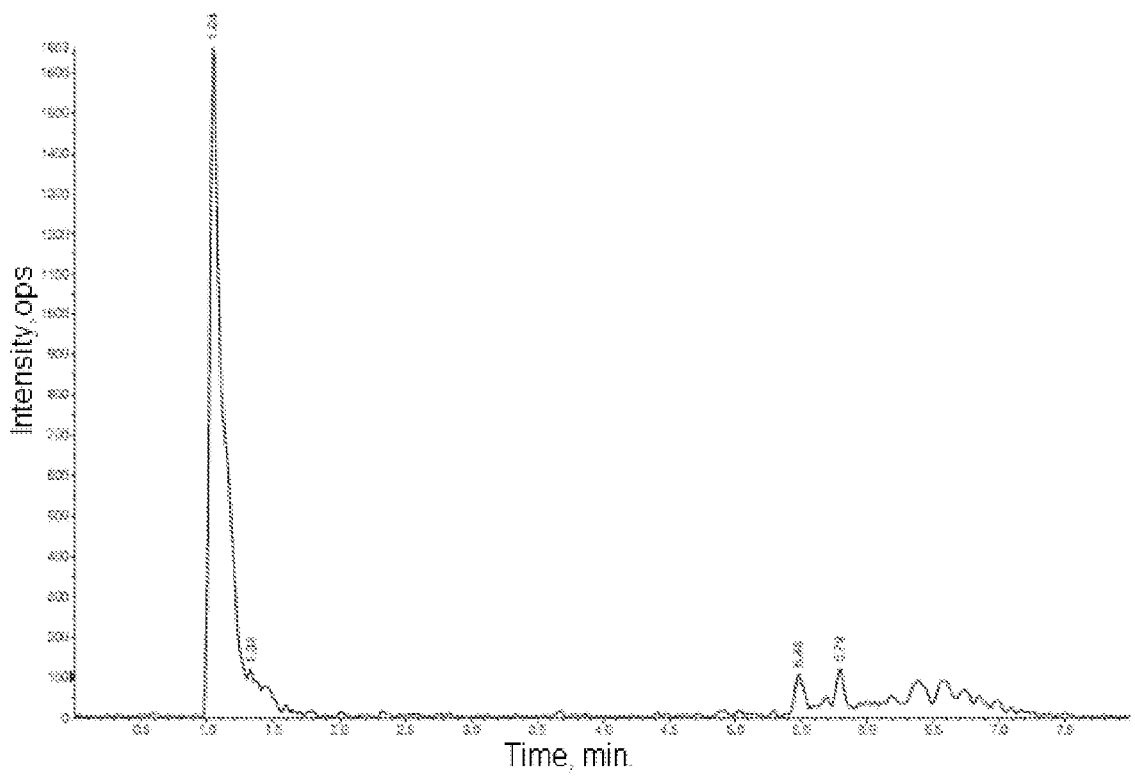

FIG. 3. HPLC profile obtained by analyzing a sample of the (treated) right eye of a mouse treated with a solution based on 1% citicoline, 0.2% hyaluronic acid and BAK 0.01%, as described in the examples. Analyzed sample profile shows the presence of a peak at an elution time of 1.04 minutes, corresponding to citicoline. In this experiment it is demonstrated the presence of significant amounts of citicoline in the posterior chamber of the treated eye.

Figure 4:
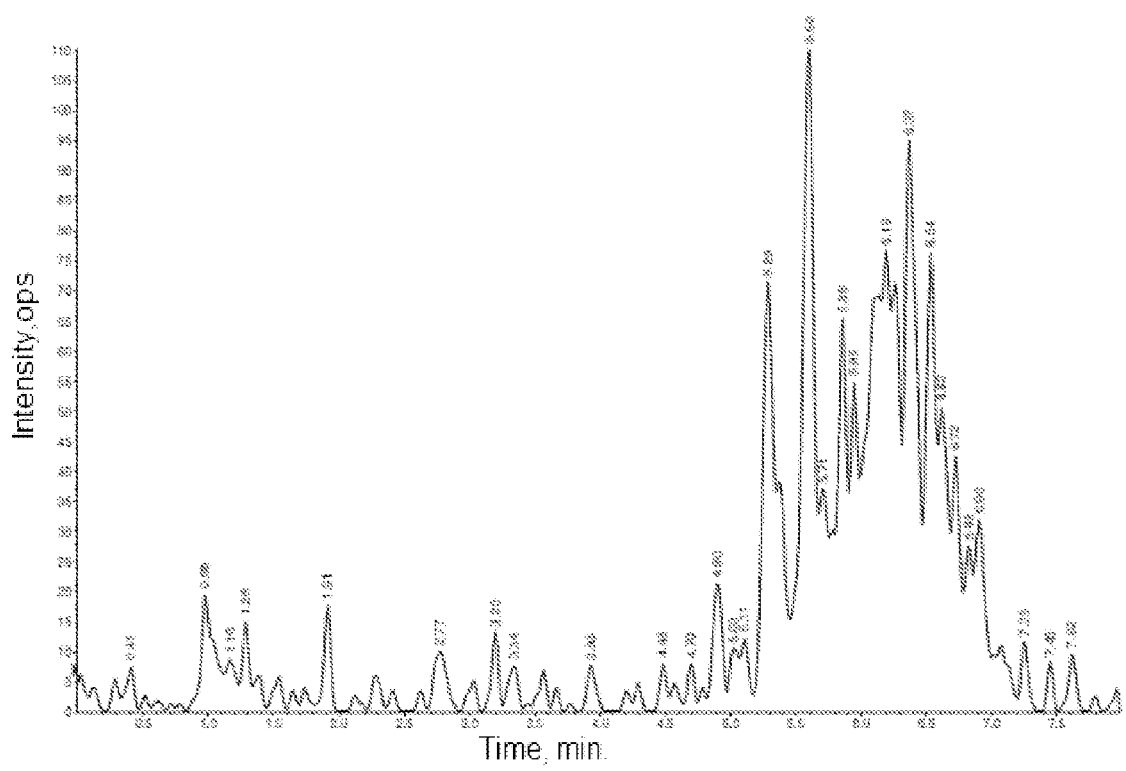

FIG. 4. HPLC profile obtained by analyzing a sample of the (contralateral) left eye of a mouse treated with a solution based on 1% citicoline, 0.2% hyaluronic acid and 0.01% BAK, as described in the examples. Analyzed sample profile does not highlight the presence of citicoline, which therefore in this experiment is unable to pass to the contralateral eye through the systemic route.

Figure 5:
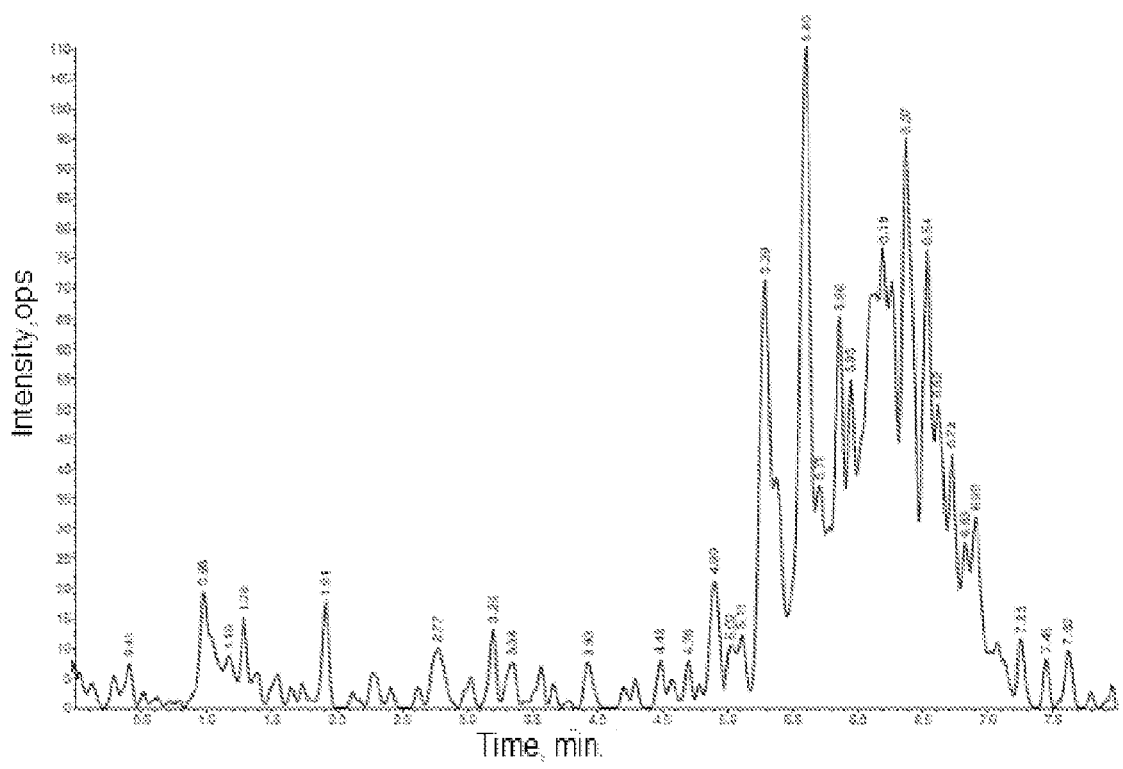

FIG. 5. HPLC profile obtained by analyzing a sample of the left eye (contralateral, right eye was lost) of a mouse used as negative control (untreated). Citicoline is not observed.

Figure 6:
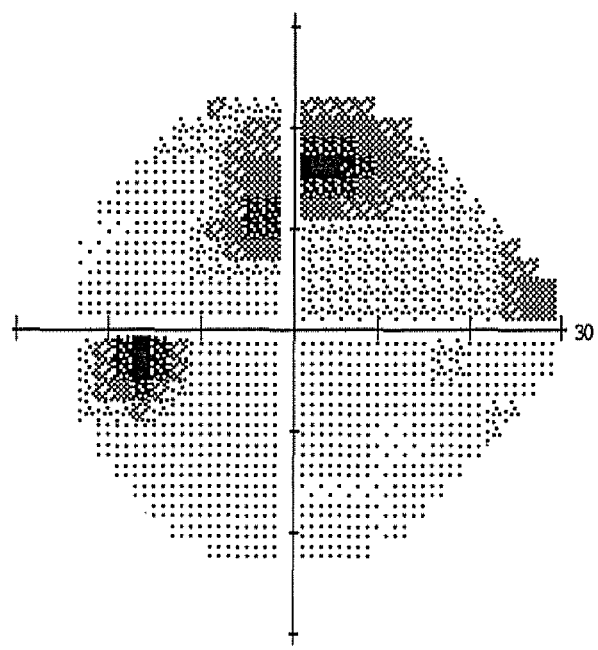

FIG. 6. Results of the campimetric test of patient 1 before treatment with the citicoline-based composition described in Example 2.

Figure 7:
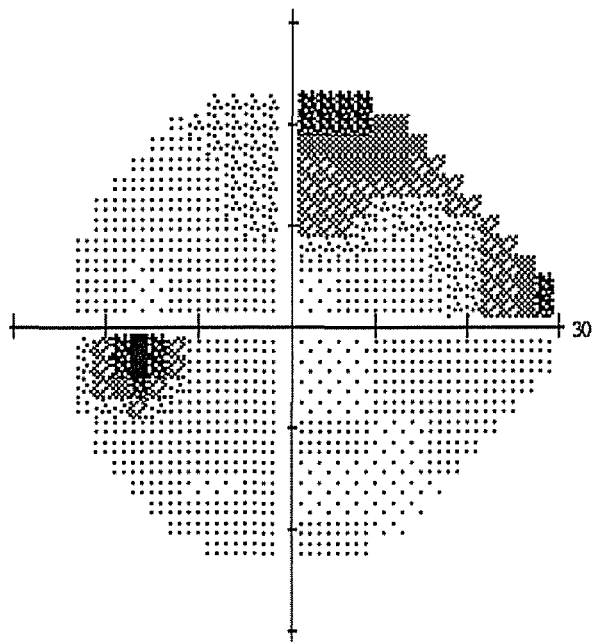

FIG. 7. Results of the campimetric test of patient 1 after treatment with the citicoline-based composition described in Example 2.

Figure 8:
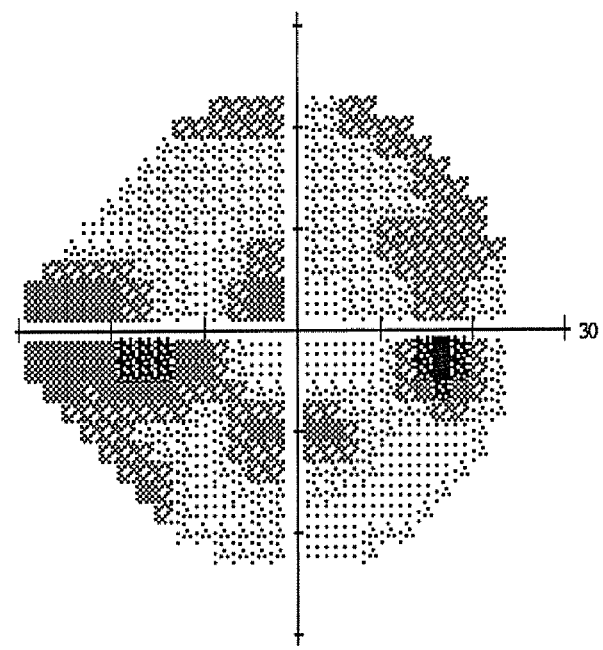

FIG. 8. Results of the campimetric test of patient 2 before treatment with the citicoline-based composition described in Example 2.

Figure 9:
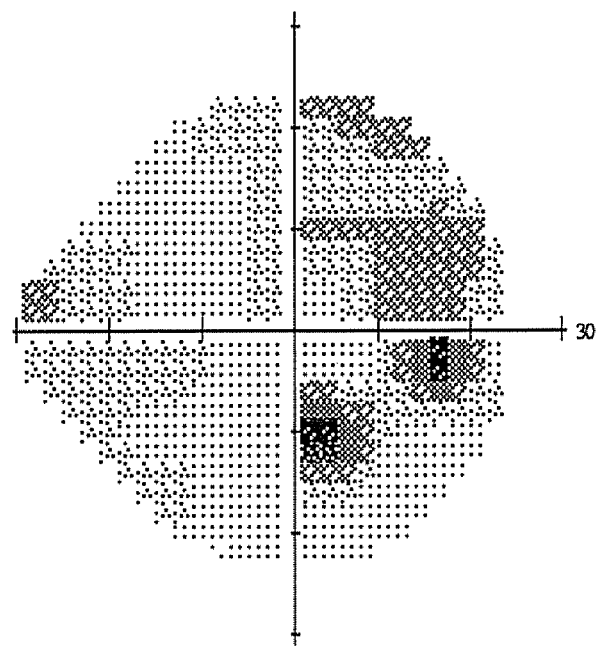

FIG. 9. Results of the campimetric test of patient 2 after treatment with the citicoline-based composition described in Example 2.

Figure 10:
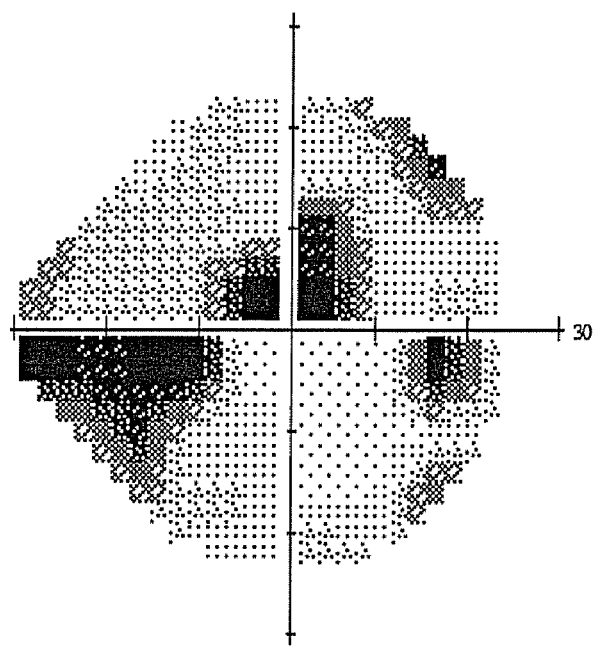

FIG. 10. Results of the campimetric test of patient 3 before treatment with the citicoline-based composition described in Example 2.

Figure 11:
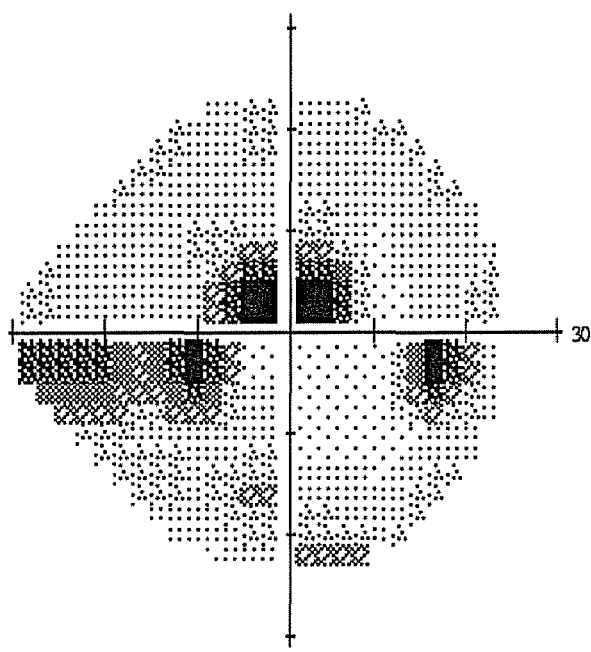

FIG. 11. Results of the campimetric test of patient 3 after treatment with the citicoline-based composition described in Example 2.

Figure 12:
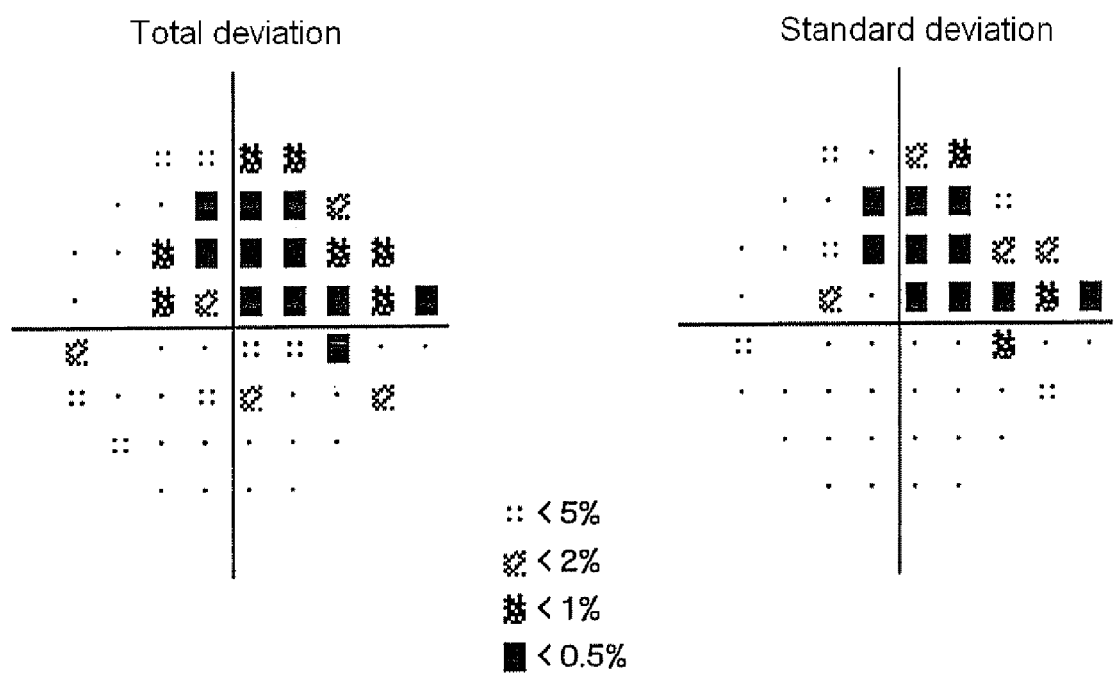

FIG. 12. Mean Deviation (MD) (indicated as standard deviation in the left-side panel) and Pattern Standard Deviation (PSD) (indicated as deviation from pattern in the right-side panel) obtained in the campimetric test of patient 1 before treatment with the citicoline-based composition described in Example 2.

Figure 13:
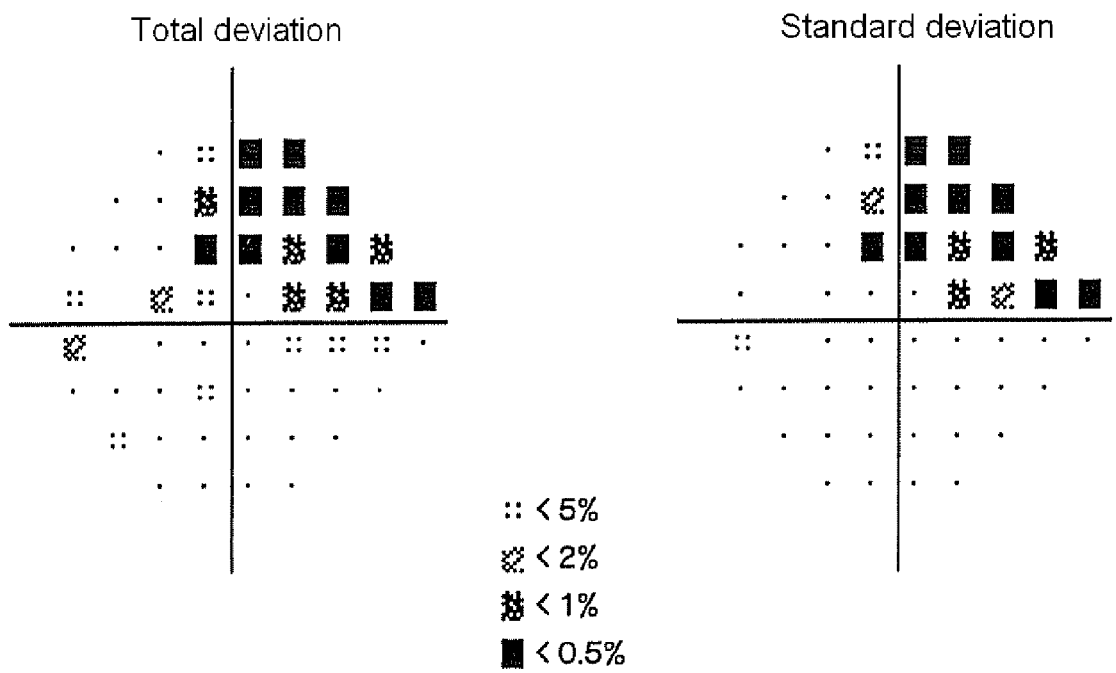

FIG. 13. Mean Deviation (MD) (indicated as standard deviation in the left-side panel) and Pattern Standard Deviation (PSD) (indicated as deviation from pattern in the right-side panel) obtained in the campimetric test of patient 1 after treatment with the citicoline-based composition described in Example 2.

Figure 14:
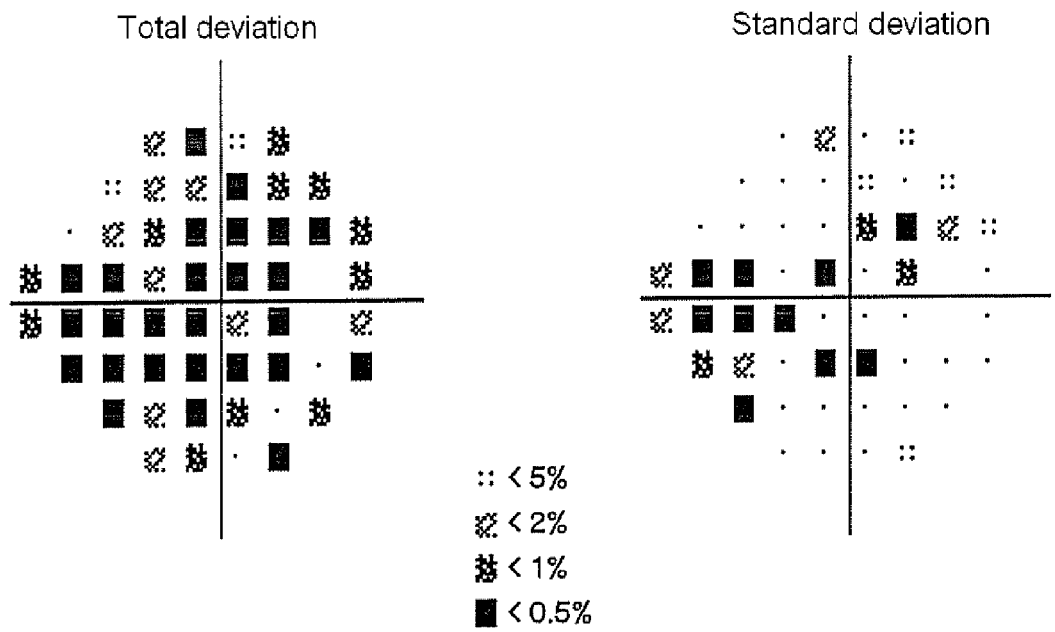

FIG. 14. Mean Deviation (MD) (indicated as standard deviation in the left-side panel) and Pattern Standard Deviation (PSD) (indicated as deviation from pattern in the right-side panel) obtained in the campimetric test of patient 2 before treatment with the citicoline-based composition described in Example 2.

Figure 15:
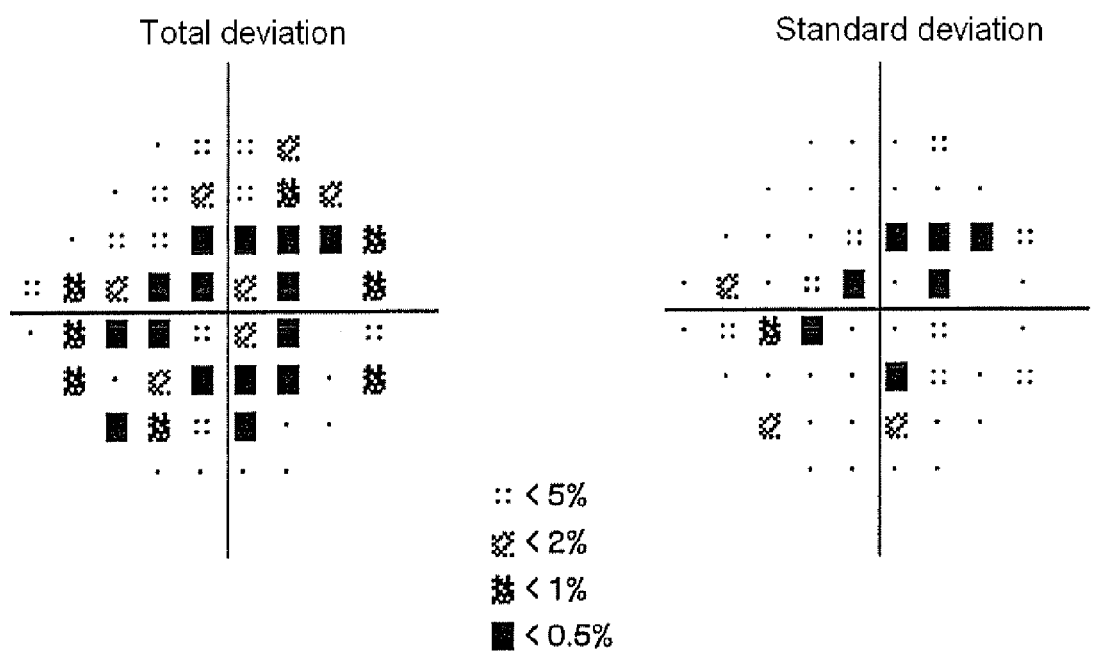

FIG. 15. Mean Deviation (MD) (indicated as standard deviation in the left-side panel) and Pattern Standard Deviation (PSD) (indicated as deviation from pattern in the right-side panel) obtained in the campimetric test of patient 1 after treatment with the citicoline-based composition described in Example 2.

Figure 16:
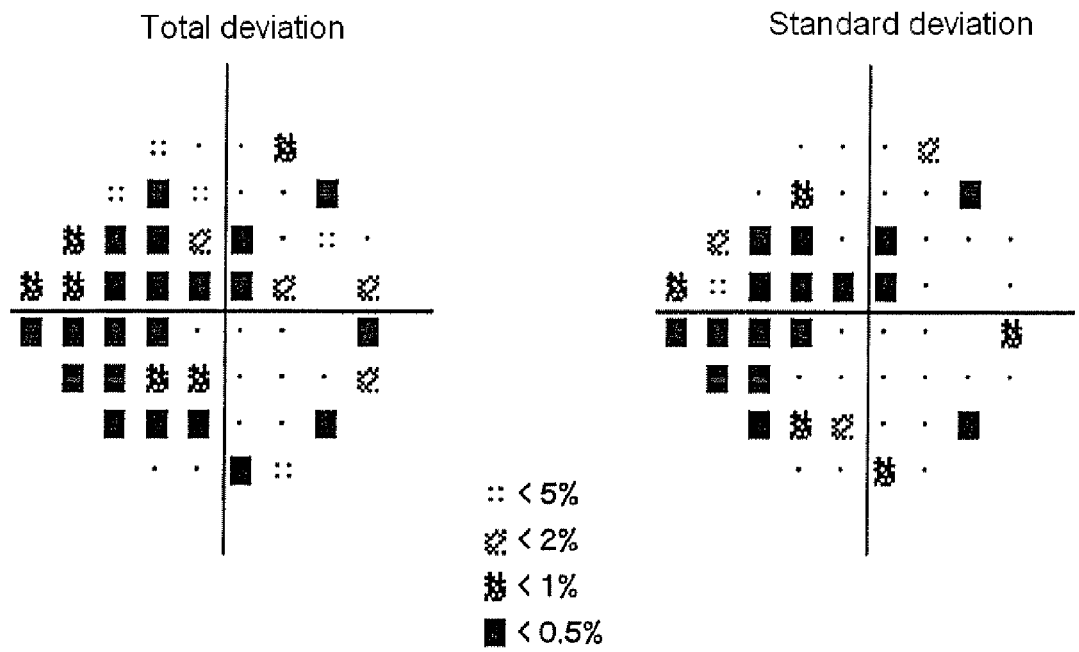

FIG. 16. Mean Deviation (MD) (indicated as standard deviation in the left-side panel) and Pattern Standard Deviation (PSD) (indicated as deviation from pattern in the right-side panel) obtained in the campimetric test of patient 3 before treatment with the citicoline-based composition described in Example 2.

Figure 17:
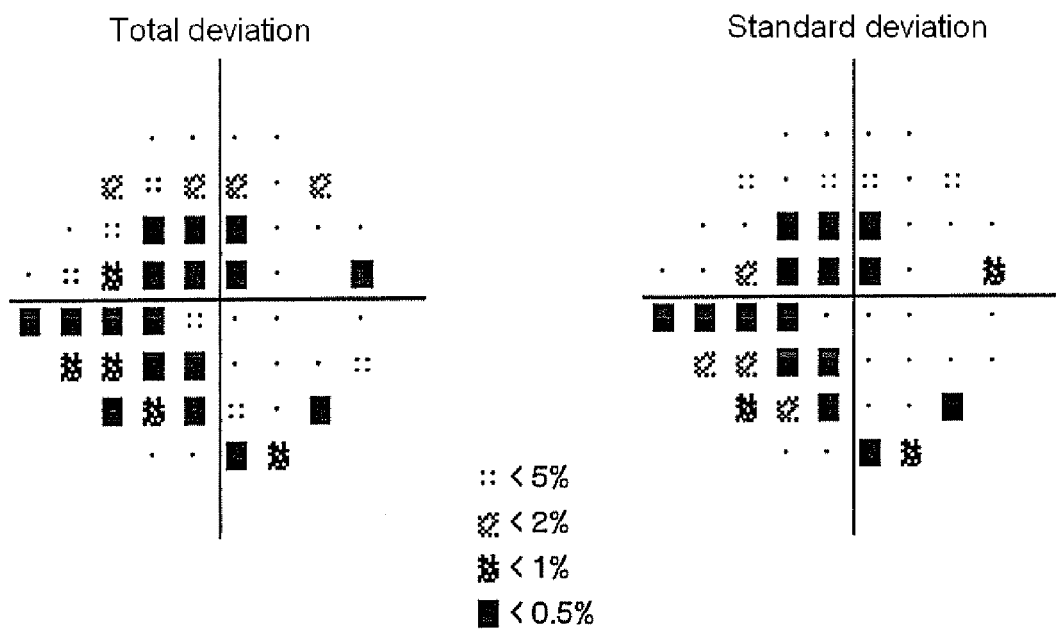

FIG. 17. Mean Deviation (MD) (indicated as standard deviation in the left-side panel) and Pattern Standard Deviation (PSD) (indicated as deviation from pattern in the right-side panel) obtained in the campimetric test of patient 3 after treatment with the citicoline-based composition described in Example 2.

DETAILED DESCRIPTION OF THE INVENTION

According to the present invention, citicoline (cytidine-5'-diphosphocholine), purchased or prepared according to protocols described in the known art, like e.g. according to Kyowa production protocol (Drug Master File citicoline Kyowa Hakko Kogyo Co., Ltd) is administered on the ocular surface of patients suffering from glaucoma and/or ocular hypertension.

Citicoline for topic use may be used in treating all different forms of glaucoma, like e.g. congenital glaucoma, open-angle glaucoma, closed-angle glaucoma and glaucoma without hypertension.

Object of the present invention are the compositions comprising citicoline for topic use in treating glaucoma and/or ocular hypertension.

Such compositions should of course comprise one or more carriers, diluents and/or excipients suitable for preparing ophthalmic compositions. Suitable for preparing ophthalmic compositions are all carriers, diluents or excipients tolerated by the eye. Examples of excipients that may be used in said compositions are Polysorbate 80, polyethylene glycol (e.g., PEG200, PEG400) dextran and the like.

Said compositions may also comprise carriers apt to increase bioavailability, stability and tolerability of the active principle. For instance, viscosity-increasing agents such as hyaluronic acid, methylcellulose, polyvinyl alcohol, polyvinyl pyrrolidone, etc. may be used.

Said compositions may comprise carriers for improving citicoline bioavailability by increasing corneal permeability, like e.g. dimethyl sulfoxide, membrane phospholipids and surfactants.

To prevent contaminations, said compositions could comprise one or more preservatives having antimicrobial activity, like e.g. benzalchonium chloride (shortened in BAK).

Citicoline concentration in said compositions is preferably comprised in the range between 5 and 30 mg per gram or ml of composition.

In accordance with the invention, citicoline is preferably used at a concentration per unit dose of between about 0.0035 and about 1.5 mg/die.

By "unit dose" it is meant the dose that is administered each time to the patient, be it subdivided into plural administrations during the day, be it daily, or be it at intervals of days.

The compositions described herein could comprise, besides citicoline, other active principles for topic use in treating glaucoma and/or ocular hypertension, like e.g. topic anti-hypertensive drugs.

Said compositions for topic use could be in any form deemed suitable by the person skilled in the art to be applied directly on the ocular surface, like e.g. solution, ointment, suspension, eye drops, gel, cream, foam, spray, liniment, powder.

Such compositions could be prepared according to the techniques known to the skilled person in the art.

The eye drops may comprise salts, such as sodium phosphate monobasic monohydrate, sodium phosphate bibasic dodecahydrate, sodium chloride or a combination thereof, and preferably may be a physiological solution with 0.9% NaCl, at a physiological pH (pH 7.0-7.4) and a physiological osmolarity (290-310 mOsm).

In a preferred embodiment the eye drops comprises citicoline between 0.5% and 3% w/v, preferably 2%, hyaluronic acid at a concentration comprised between 0.1% and 0.3%, preferably 0.2%, benzalchonium chloride at a concentration comprised between 0.005 and 0.02%, preferably 0.01%.

The Inventors, as described in detail in the Examples section, have surprisingly observed that administration on the ocular surface of citicoline in association with hyaluronic acid and benzalchonium chloride, preferably in the form of eye drops and in the concentrations described herein, causes optimal absorption of the active principle in the posterior segment of the eye (vitreous chamber).

Compositions in the form of emulsions may be O/W (Oil/Water) or W/O or W/O/W and O/W/O, better if micro or nanoemulsions, but may also be colloidal dispersions or solutions. Microemulsions may be proposed as gels, creams, or even in the form of foams. All known surfactants, like e.g. the siliconic, glucosidic and phospholipidic ones, may be used for preparing emulsions.

The present invention also provides a method for treating glaucoma and/or ocular hypertension comprising administration, to patients needing it, of effective amounts of a composition as described herein.

Said glaucoma forms can be selected in the group comprising congenital glaucoma, open-angle glaucoma, closed-angle glaucoma and glaucoma without hypertension.

In the treating method, the exact dose and the frequency of administration of the compositions will depend on the specific severity of the condition to be treated, on the age, weight and general physical conditions of the specific patient, as is well-known to those skilled in the art.

Some effective doses that can be administered are indicated hereinafter:
they could be administered at a unit dose comprised between about 0.0035 and about 1.5 mg/die, optionally in combination with one or more compounds for treating glaucoma, like e.g. topic anti-hypertensive drugs whose unit dose could be of about 100%, about 90%, about 80%, about 70%, about 60%, about 50%, about 40%, about 30% or less with respect to the unit doses commonly used in therapy against glaucoma.

Hereinafter the description is described in detail in the following examples, which have a purely illustrative purpose without limiting the scope of protection granted.

EXAMPLES

Example 1

Protocol for Preparing Eye Drops Comprising 1% w/v Citicoline

Components were dissolved in an adequate amount of water at the following concentrations: 0.01% sodium phosphate monobasic monohydrate, 0.1% sodium phosphate bibasic dodecahydrate, 0.7% sodium chloride, 0.2% hyaluronic acid, purified water q.s. to 100%. Then 1% citicoline was added, adding each component upon dissolution of the preceding one. 0.01% BAK (Benzalchonium chloride) was dissolved in a small volume of distilled water heated to 70° C., and this solution was added to the previously prepared solution. Spontaneous pH was controlled; it stabilized within the required values, i.e. between 7.0 and 7.2, and then the solution was brought to volume.

Example 2

Protocol for Preparing Eye Drops Comprising 2% w/v Citicoline

Components were dissolved in an adequate amount of water at the following concentrations: 0.01% sodium phosphate monobasic monohydrate, 0.1% sodium phosphate bibasic dodecahydrate, 0.65% sodium chloride, 0.2% hyaluronic acid, purified water q.s. to 100%. Then, 2% citicoline was added, adding each component upon dissolution of the preceding one. 0.01% BAK (Benzalchonium chloride) was dissolved in a small volume of distilled water heated to 70° C., this solution was added to the previously prepared solution. Spontaneous pH was controlled; it settled within the required values, i.e. between 7.0 and 7.2, then the solution was brought to volume.

Example 3

Studies on Citicoline Crossing of Ocular Tissues

Citicoline Administration to Mice.
The experiment was carried out on five CD-1 line mice (weight of each mouse: about 30 g) so divided:
a) 2 mice were treated with the eye drops prepared as described in example 1, comprising 1% citicoline.
b) 2 mice were treated with the eye drops prepared as described in example 2, comprising 2% citicoline.
c) 1 untreated control mouse.
The right eye of each mouse was treated with 2 drops of ophthalmic solution 2 times a day for three days.
Preparation of Samples to be Analyzed
On the fourth day, after sacrificing the animals, their eyes were collected, rinsed in physiological solution and thus stored on ice:
Group a): mouse 1: whole RE (RE=right eye) in PBS (phosphate buffer solution) solution; whole LE (LE=left eye) in PBS solution; mouse 2: RE in suspension, washed with 1.5 mL of PBS; LE in suspension, washed with 1.5 mL of PBS.
Group b): mouse 1: whole RE in PBS solution; whole LE in PBS solution; mouse 2: RE in suspension, washed with 1.5 mL of PBS; LE in suspension, washed with 1.5 mL of PBS.
Group c) whole RE in PBS solution; whole LE in PBS solution.
In laboratory, suspensions were deemed useless for analysis owing to excessive dilution, therefore only whole eyes were used as follows:
  vitreous humor was sucked out with an 100 µL SGE-type syringe and diluted with 20 µL of distilled water;
  diluted vitreous humor was centrifuged;
  to the collected surnatant, 50 µL of a 50% water and 50% methanol solution were added;
  passing through vortex;
Then, samples thus prepared were analyzed by liquid chromatography and mass spectrometry (LC-MS/MS).
Mass Spectrometry (LC-MS/MS) Analysis of Citicoline Presence in Samples.
Samples analyzed by mass spectrometry (LC-MS/MS) yielded the following results:
Sample 1) RE of mouse treated with 2% citicoline=molecule is visible (FIG. 1)
Sample 2) LE of mouse treated with 2% citicoline=molecule is visible (FIG. 2)
Sample 3) RE of mouse treated with 1% citicoline=molecule is visible (FIG. 3)
Sample 4) LE of mouse treated with 1% citicoline=molecule is NOT visible (FIG. 4)
Sample 5) control LE (RE was lost)=MOLECULE IS NOT VISIBLE (FIG. 5). Citicoline-matching peak in HPLC profile was identified by mass spectrometry and by comparing obtained HPLC profiles (FIGS. 1-5) with that obtained by using a standard citicoline sample.
Conclusions on results obtained:
  the machine reads the molecule with a high certainty, as the signal is present always at the same times and in all of the 4 transitions used;
  between samples the machine always performed blank readings, in order to prevent contamination;
  between 1% and 2% concentrations there is a difference concerning systemic absorption, which is less for the lower concentration, as not visible in the left eye.
  the molecule, carried with the solution at issue, reaches the vitreous humor.
Clinical Testing
Action of a citicoline-based composition, administered by topic ocular route in patients suffering from simple chronic glaucoma and under hypotonizing ocular therapy, was assessed. In these patients, to the standard ocular hypotensive therapy the citicoline-based composition in eye drops described in Example 2 was added, with a posology of 1 instillation 3 times a day for at least 1 month. It was observed how, though ocular pressure underwent no modification whatsoever, after only one month of treatment the visual field exhibited significant improvements in all patients treated. In particular, a marked improvement was witnessed for all 3 of the cases treated, as is evident from the results of the campimetric test of the sensitivity scale (Grey Scale, see FIGS. 6-11), the Mean Deviation (MD) and the Pattern Standard Deviation (PSD) (see Table 1 and FIGS. 12-17). The definition and interpretation of these parameters is known to the skilled person in the art.

TABLE 1

| Clinical Cases | basal MD | MD after 1 month of treatment | basal PSD | PSD after 1 month of treatment |
| --- | --- | --- | --- | --- |
| Patient # 1 | −5.32 dB | −3.97 dB | 6.23 dB | 4.77 dB |
| Patient # 2 | −8.94 dB | −5.76 dB | 5.83 dB | 4.94 dB |
| Patient # 3 | −10.39 dB | −8.06 dB | 12.15 dB | 10.25 dB |

Discussion on Data Yielded by Clinical Testing.
No ocular pressure modification was found, highlighting change of visual fields to be due to a direct action of citicoline on the optic nerve. This data was observed when the drug was administered at doses 40 times higher by systemic route, and had never been observed with a topic administration in eye drops. To sum up, we can state that in these patients administration of citicoline in eye drops showed an improvement in the visual field of patients suffering from glaucoma, and that such a clinical benefit is ascribable to its action on the optic nerve head. Such action has a dose/effect ratio markedly greater than that present in the literature with IM-, IV- and oral administration, and the effect is quicker.

REFERENCE

1. Grieb P. et al, Pharmacodynamics of citicoline relevant to the treatment of glaucoma. J Neurosci Res 2002; 67:143-148

2. Burgoyne F C et al, The optic nerve head as a biomechanical structure: a new paradigm for understanding the role of IOP-related stress and strain in the pathophysiology of glaucomatous optic nerve head damage. Prog Retin Eye Res 2005; 24(1):39-73
3. Citicoline, monograph Altern Med Rev 2008; 13(1):50-57
4. Oshitari T, Fujimoto N, Adachi-Usami E., Citicoline has a protective effect on damaged retinal ganglion cells in mouse culture retina. Neuroreport 2002; 13(16):2109-2111.
5. Pecori Giraldi J et al, Therapeutic value of citicoline in the treatment of glaucoma (computerized and automated perimetric investigation). Intern Ophth 1989; 13:109-112
6. Parisi V et al, Cytidine-5'-diphosphocholine (citicoline) improve retinal and cortical responses in patients with glaucoma. Ophth 1999; 106:1126-1134
7. Rejadak R et al, Oral citicoline treatment improve visual pathway function in glaucoma. Med Sci Monit 2003; 9(3): P124-28
8. Parisi V, Electrophysiological assessment of glaucomatous visual dysfunction during treatment with cytidine-5'-diphosphocholine (citicoline): a study of 8 years of follow-up.
9. Parisi V et al, Evidence of the neuroprotective role of citicoline in glaucoma patients. Prog in Brain Res 2008; 173:541-54
10. Rejadak R, Citicoline treatment increases retinal dopamine content in rabbits. Ophthalmic Res 2002; 34:146-49
11. Chan KC et al, Proton magnetic resonance spectroscopy revealed choline reduction in the visual cortex in an experimental model of chronic glaucoma. Exp Eye Res 2009; 88:65-70

The invention claimed is:

1. A method of using citicoline, the method comprising administering topically an ophthalmic composition comprising citicoline and one or more carriers to a patient for treatment of glaucoma and/or ocular hypertension.

2. The method according to claim 1, wherein said composition further comprises one or more diluents and/or excipients.

3. The method according to claim 1, wherein said composition has a concentration of between 5 mg and 30 mg citicoline per gram or milliliter.

4. The method according to claim 1, wherein said citicoline in a unit dose is between 0.0035 mg and 1.5 mg per day.

5. The method according to claim 1, wherein said one or more carriers is hyaluronic acid.

6. The method according to claim 2, wherein said one or more excipients is benzalchonium chloride.

7. The method according to claim 1, wherein said composition further comprises one or more active principles for topical use in treating glaucoma and/or ocular hypertension.

8. The method according to claim 1, wherein said composition is in a form selected from the group consisting of: solution, ointment, suspension, eye drops, gel, cream, foam, spray, liniment, and powder.

9. The method according to claim 8, wherein said composition is in the form of eye drops and said (i) citicoline is in a concentration between 0.5% w/v and 3% w/v.

10. The method according to claim 9, wherein said composition is comprised of (ii) benzalchonium chloride in a concentration between 0.005% w/v and 0.02% w/v and (iii) hyaluronic acid in a concentration between 0.1% w/v and 0.3% w/v.

11. The method according to claim 9, wherein said patient is treated for glaucoma.

12. The method according to claim 10, wherein said patient is treated for glaucoma.

13. The method according to claim 9, wherein said patient is treated for ocular hypertension.

14. The method according to claim 10, wherein said patient is treated for ocular hypertension.

* * * * *